US011541778B2

(12) United States Patent
Ferguson et al.

(10) Patent No.: US 11,541,778 B2
(45) Date of Patent: Jan. 3, 2023

(54) THERMAL RUNAWAY DETECTION AND MITIGATION FOR ELECTRIC VEHICLES

(71) Applicant: GM Cruise Holdings LLC, San Francisco, CA (US)

(72) Inventors: Kenneth Ramon Ferguson, Scottsdale, AZ (US); Erik Nielsen, Glendale, AZ (US); Chase Kaufman, Fountain Hills, AZ (US)

(73) Assignee: GM Cruise Holdings LLC, San Francisco, CA (US)

( * ) Notice: Subject to any disclaimer, the term of this patent is extended or adjusted under 35 U.S.C. 154(b) by 229 days.

(21) Appl. No.: 16/787,824

(22) Filed: Feb. 11, 2020

(65) Prior Publication Data

US 2021/0245627 A1 Aug. 12, 2021

(51) Int. Cl.
B60L 58/26 (2019.01)
H01M 10/613 (2014.01)
(Continued)

(52) U.S. Cl.
CPC ............ B60L 58/26 (2019.02); B60L 50/64 (2019.02); B60Q 9/00 (2013.01); B60S 5/00 (2013.01); B60W 60/001 (2020.02); G01N 33/0063 (2013.01); G01R 31/371 (2019.01); G01R 31/382 (2019.01); G01R 31/396 (2019.01); G05D 1/0212 (2013.01);
(Continued)

(58) Field of Classification Search
CPC ...... G05D 1/00; G05D 1/0212; G05D 1/0291; G05D 1/02; G01N 33/00; G01N 33/0063; B60S 5/00; B60Q 9/00; B60W 60/001; B60W 2510/246; B60W 60/00; G01R 31/396; G01R 31/382; G01R 31/371; H01M 10/00; H01M 10/482; H01M 10/486; H01M 10/613; H01M 10/625; H01M 10/633; H01M 10/6567; H01M 2220/20; H01M 10/48; B60L 50/64; B60L 58/26
USPC .......................................................... 701/22
See application file for complete search history.

(56) References Cited

U.S. PATENT DOCUMENTS 6,204,769 B1    3/2001  Arai et al.
9,227,484 B1 *  1/2016  Justice ............... B60H 1/00742
(Continued)

FOREIGN PATENT DOCUMENTS

CN    106627218 A  *  5/2017
CN    106816668 A     6/2017

OTHER PUBLICATIONS

PCT International Search Report and Written Opinion issued in PCT/US2020/066321 dated May 31, 2021; 19 pages.
(Continued)

Primary Examiner — Anthony R Jimenez
(74) Attorney, Agent, or Firm — Akona IP PC

(57) ABSTRACT

A system for mitigating thermal runaway in a battery-powered electric vehicle (EV). The system includes a gas sensor configured to measure a level of at least one type of gas in a vicinity of a battery of the EV, a thermal event detector configured to determine, based on the measured level of the at least one type of gas, that the battery is experiencing out-gassing, and a communications interface configured to transmit an alert to a fleet management system regarding the out-gassing of the battery. The fleet management system alters an assignment of the EV in response to the out-gassing of the battery.

20 Claims, 4 Drawing Sheets

(51) Int. Cl.
*H01M 10/625* (2014.01)
*H01M 10/633* (2014.01)
*H01M 10/6567* (2014.01)
*G01R 31/396* (2019.01)
*G01R 31/382* (2019.01)
*G01R 31/371* (2019.01)
*B60L 50/64* (2019.01)
*B60W 60/00* (2020.01)
*B60Q 9/00* (2006.01)
*B60S 5/00* (2006.01)
*G01N 33/00* (2006.01)
*G05D 1/02* (2020.01)
*H01M 10/48* (2006.01)

(52) U.S. Cl.
CPC ........ *G05D 1/0291* (2013.01); *H01M 10/482* (2013.01); *H01M 10/486* (2013.01); *H01M 10/613* (2015.04); *H01M 10/625* (2015.04); *H01M 10/633* (2015.04); *H01M 10/6567* (2015.04); *B60W 2510/246* (2013.01); *H01M 2220/20* (2013.01)

(56) References Cited

U.S. PATENT DOCUMENTS

| | | | |
|---|---|---|---|
| 9,387,928 B1* | 7/2016 | Gentry | G08G 5/0052 |
| 9,673,492 B2* | 6/2017 | Nemesh | H01M 10/625 |
| 2011/0059341 A1 | 3/2011 | Matsumoto et al. | |
| 2013/0314094 A1* | 11/2013 | Farmer | G01N 29/14 |
| | | | 324/430 |
| 2017/0057497 A1* | 3/2017 | Laur | G06K 9/00348 |
| 2018/0102572 A1* | 4/2018 | Wedig | H02J 9/061 |

OTHER PUBLICATIONS

Larsson, F., "Research Institutes of Sweden Thermal Propagation in Lithium-Ion Batteries," pp. 1-31 (Mar. 31, 2018).

PCT Invitation to Pay Additional Fees issued in PCT/US2020/066321 dated Mar. 29, 2021; 13 pages.

* cited by examiner

THERMAL RUNAWAY DETECTION AND MITIGATION FOR ELECTRIC VEHICLES

TECHNICAL FIELD OF THE DISCLOSURE

The present disclosure relates generally to battery-powered electric vehicles and, more specifically, to devices and methods for detecting and mitigating thermal runaway in battery-powered vehicles.

BACKGROUND

The batteries that power electric vehicles, such as lithium-ion batteries, can experience thermal runaway, which can lead to battery and vehicle fires. During thermal runaway, an increase in temperature in a battery cell increases the rate of exothermic reactions within the cell, which in turn causes the temperature to rise further in an unrestrained manner. Current methods to detect thermal runaway include measuring the temperature around the battery. However, once the battery temperature rises above a threshold level for detecting thermal runaway, the reactions may have already advanced to a point that the thermal runaway cannot be constrained.

BRIEF DESCRIPTION OF THE DRAWINGS

To provide a more complete understanding of the present disclosure and features and advantages thereof, reference is made to the following description, taken in conjunction with the accompanying figures, wherein like reference numerals represent like parts, in which.

DESCRIPTION OF EXAMPLE EMBODIMENTS OF THE DISCLOSURE

Overview

Figure 1:
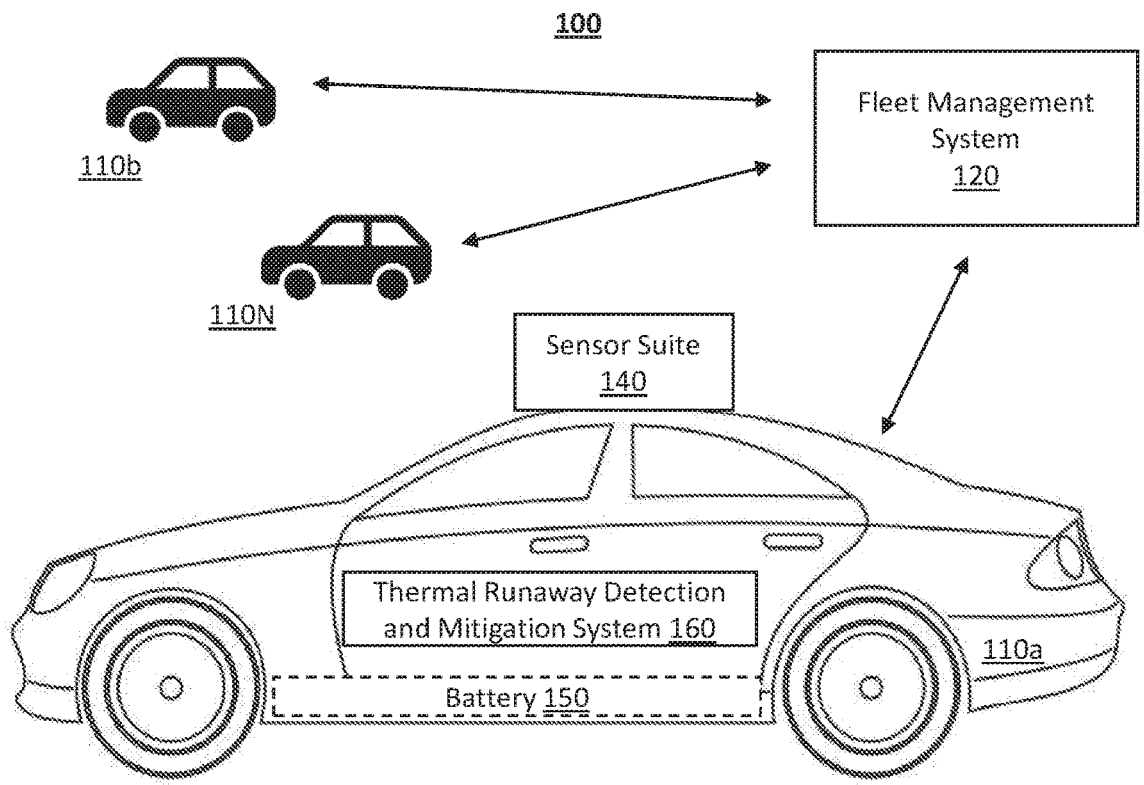
FIG. 1 is a block diagram illustrating a system including an example EV in a fleet of EVs in which thermal runaway detection and mitigation according to some embodiments of the present disclosure may be implemented.

The systems, methods and devices of this disclosure each have several innovative aspects, no single one of which is solely responsible for the all of the desirable attributes disclosed herein. Details of one or more implementations of the subject matter described in this specification are set forth in the description below and the accompanying drawings.

Electric vehicle batteries can experience thermal runaway, which damages the batteries and can lead to vehicle fires. During a thermal runaway event, chemical reactions within a battery release gasses, such as hydrogen, carbon monoxide, carbon dioxide, and various hydrocarbons, that are not released during normal operation of the battery, or that are released at higher rates or in higher concentration than during normal operation of the battery. This release of gasses is referred to as out-gassing. The presence or concentration of certain gasses associated with out-gassing reactions can indicate the start of a thermal runaway event. By detecting in a change in the levels of one or more gasses around the battery, a potential thermal runaway event can be detected earlier than in prior methods for detecting thermal runaway. Data from additional sensors in or around electric vehicle batteries, such as pressure, voltage, current, and/or temperature sensors, can further enable early detection of thermal runaway. Early detection of out-gassing and potential thermal runaway events allows fire suppression and risk mitigation techniques to be applied sooner.

In vehicle fleets, such as fleets of autonomous vehicles (AVs), the risk mitigation techniques can include fleet-based responses. For example, if a vehicle that was previously assigned to a task (e.g., to pick up and deliver an item, or to provide a ride to a user) experiences thermal runaway, a fleet management system can automatically assign a different AV to take over the task. The fleet management system can instruct the AV that has experienced thermal runaway to discontinue its assignment and autonomously maneuver to a safe location away from people or property, such as an empty parking lot. If the thermal runaway occurs in a vehicle facility, such as an EV charging station, the fleet management system can take actions to protect other vehicles in the fleet, e.g., by deploying firewalls around the vehicle experiencing thermal runaway, or by instructing other vehicles to autonomously maneuver away from the vehicle experiencing thermal runaway.

Embodiments of the present disclosure provide a system for mitigating thermal runaway in a battery-powered electric vehicle (EV). The system includes a gas sensor, a thermal event detector, and a communications interface. The gas sensor is configured to measure a level of at least one type of gas in the vicinity of the battery of the EV. The thermal event detector is configured to determine, based on the measured level of the at least one type of gas, that the battery is experiencing out-gassing. The communications interface is configured to transmit an alert to a fleet management system regarding the out-gassing of the battery, and the fleet management system is configured to alter an assignment of the EV in response to the out-gassing of the battery.

Embodiments of the present disclosure also provide a method for mitigating thermal runaway in a battery-powered EV. The method includes measuring a level of a type of gas in a vicinity of a battery of the EV; determining, based on the measured level of the type of gas, that the battery is experiencing out-gassing; transmitting an alert to a fleet management system indicating that the battery is experiencing out-gassing; and altering, by the fleet management system, an assignment of the EV in response to the alert.

Embodiments of the present disclosure further provide a system for suppressing thermal runaway in a battery-powered EV. The system includes a gas sensor, a thermal event detector, a cooling system, and a communications interface. The gas sensor is configured to measure a level of at least one type of gas in a vicinity of a battery of the EV. The thermal event detector is configured to determine, based on the measured level of the at least one type of gas, that the battery is experiencing out-gassing. The cooling system is configured to apply a coolant stored on the EV to the battery in response to the determination by the thermal event detector that the battery is experiencing out-gassing. The communications interface is configured to transmit an alert to a fleet management system regarding the out-gassing of the battery.

As will be appreciated by one skilled in the art, aspects of the present disclosure, in particular aspects of fire detection and mitigation for electric vehicles, described herein, may be embodied in various manners (e.g., as a method, a system, a computer program product, or a computer-readable storage medium). Accordingly, aspects of the present disclosure may take the form of an entirely hardware embodiment, an entirely software embodiment (including firmware, resident software, micro-code, etc.) or an embodiment combining software and hardware aspects that may all generally be referred to herein as a "circuit," "module" or "system." Functions described in this disclosure may be implemented as an algorithm executed by one or more hardware processing units, e.g. one or more microprocessors, of one or more computers. In various embodiments, different steps and portions of the steps of each of the methods described herein may be performed by different processing units. Furthermore, aspects of the present disclosure may take the form of a computer program product embodied in one or more computer-readable medium(s), preferably non-transitory, having computer-readable program code embodied, e.g., stored, thereon. In various embodiments, such a computer program may, for example, be downloaded (updated) to the existing devices and systems (e.g. to the existing perception system devices and/or their controllers, etc.) or be stored upon manufacturing of these devices and systems.

The following detailed description presents various descriptions of specific certain embodiments. However, the innovations described herein can be embodied in a multitude of different ways, for example, as defined and covered by the claims and/or select examples. In the following description, reference is made to the drawings where like reference numerals can indicate identical or functionally similar elements. It will be understood that elements illustrated in the drawings are not necessarily drawn to scale. Moreover, it will be understood that certain embodiments can include more elements than illustrated in a drawing and/or a subset of the elements illustrated in a drawing. Further, some embodiments can incorporate any suitable combination of features from two or more drawings.

The following disclosure describes various illustrative embodiments and examples for implementing the features and functionality of the present disclosure. While particular components, arrangements, and/or features are described below in connection with various example embodiments, these are merely examples used to simplify the present disclosure and are not intended to be limiting. It will of course be appreciated that in the development of any actual embodiment, numerous implementation-specific decisions must be made to achieve the developer's specific goals, including compliance with system, business, and/or legal constraints, which may vary from one implementation to another. Moreover, it will be appreciated that, while such a development effort might be complex and time-consuming; it would nevertheless be a routine undertaking for those of ordinary skill in the art having the benefit of this disclosure.

In the Specification, reference may be made to the spatial relationships between various components and to the spatial orientation of various aspects of components as depicted in the attached drawings. However, as will be recognized by those skilled in the art after a complete reading of the present disclosure, the devices, components, members, apparatuses, etc. described herein may be positioned in any desired orientation. Thus, the use of terms such as "above", "below", "upper", "lower", "top", "bottom", or other similar terms to describe a spatial relationship between various components or to describe the spatial orientation of aspects of such components, should be understood to describe a relative relationship between the components or a spatial orientation of aspects of such components, respectively, as the components described herein may be oriented in any desired direction. When used to describe a range of dimensions or other characteristics (e.g., time, pressure, temperature, length, width, etc.) of an element, operations, and/or conditions, the phrase "between X and Y" represents a range that includes X and Y.

Other features and advantages of the disclosure will be apparent from the following description and the claims.

Example EV Configured for Thermal Runaway Detection and Mitigation

FIG. 1 is a block diagram illustrating a system 100 including an example EV in a fleet of EVs in which thermal runaway detection and mitigation according to some embodiments of the present disclosure may be implemented. The system 100 includes a fleet of electric vehicles (EVs) 110, including EV 110a, EV 110b, and EV 110N, and a fleet management system 120. For example, a fleet of EVs may include a number N of EVs, e.g., EV 110a through EV 110N. Some or all of the EVs 110 may be autonomous vehicles (AVs). EV 110a includes a sensor suite 140, a battery 150, and a thermal runaway detection and mitigation system 160. EVs 110b through 110N also include the sensor suite 140, battery 150, and thermal runaway detection and mitigation system 160. A single EV in the fleet is referred to herein as EV 110, and the fleet of EVs is referred to collectively as EVs 110. The thermal runaway detection and mitigation system 160 enables an EV 110 to automatically determine if it is experiencing a thermal runaway event, or is at risk of experiencing thermal runaway, and to take steps to mitigate the thermal runaway event. The fleet management system 120 may assist in mitigating the thermal runaway event, e.g., to protect other vehicles in the fleet, and to ensure tasks assigned to the EV fleet are still performed.

In some embodiments, each EV 110 is a fully autonomous electric automobile. In other embodiments, each EV 110 may additionally or alternatively be another semi-autonomous or fully autonomous vehicle; e.g., a boat, an unmanned aerial vehicle, a driverless car, etc. Additionally, or alternatively, the EV 110 may be a vehicle that switches between a semi-autonomous state and a fully autonomous state and thus, the EV may have attributes of both a semi-autonomous vehicle and a fully autonomous vehicle depending on the state of the vehicle. In some embodiments, some or all of the EVs 110 are non-autonomous electric vehicles.

In embodiments where the EVs 110 are autonomous, each EV 110 may include a throttle interface that controls an engine throttle, motor speed (e.g., rotational speed of electric motor), or any other movement-enabling mechanism; a brake interface that controls brakes of the EV (or any other movement-retarding mechanism); and a steering interface that controls steering of the EV (e.g., by changing the angle of wheels of the EV). The EV 110 may additionally or alternatively include interfaces for control of any other vehicle functions; e.g., windshield wipers, headlights, turn indicators, air conditioning, etc.

The EV 110 includes a sensor suite 140, which includes a computer vision ("CV") system, localization sensors, and driving sensors. For example, the sensor suite 140 may include photodetectors, cameras, radar, sonar, lidar, GPS, wheel speed sensors, inertial measurement units (IMUS), accelerometers, microphones, strain gauges, pressure monitors, barometers, thermometers, altimeters, ambient light sensors, etc. The sensors may be located in various positions in and around the EV 110.

An onboard computer (not shown in FIG. 1) is connected to the sensor suite 140 and functions to control the EV 110 and to process sensed data from the sensor suite 140 and/or other sensors in order to determine the state of the EV 110. Based upon the vehicle state and programmed instructions, the onboard computer modifies or controls behavior of the EV 110. The onboard computer is preferably a general-purpose computer adapted for I/O communication with vehicle control systems and sensor suite 140, but may additionally or alternatively be any suitable computing device. The onboard computer is preferably connected to the Internet via a wireless connection (e.g., via a cellular data connection). Additionally or alternatively, the onboard computer may be coupled to any number of wireless or wired communication systems.

The battery 150 is a rechargeable battery that powers the EV 110. The battery 150 may be a lithium-ion battery, a lithium polymer battery, a lead-acid battery, a nickel-metal hydride battery, a sodium nickel chloride ("zebra") battery, a lithium-titanate battery, or another type of rechargeable battery. In some embodiments, the EV 110 is a hybrid electric vehicle that also includes an internal combustion engine for powering the EV 110, e.g., when the battery 150 has low charge.

The thermal runaway detection and mitigation system 160 detects thermal runaway of the battery 150 and mitigates risks associated with thermal runaway. The thermal runaway detection and mitigation system 160 includes battery sensors, such as gas sensors, that obtain measurements of the battery 150, e.g., gas levels near the battery 150. The thermal runaway detection and mitigation system 160 processes signals received from the battery sensors to determine whether the battery 150 is at risk of experiencing thermal runaway, or is experiencing thermal runaway. If thermal runaway is detected, the thermal runaway detection and mitigation system 160 may apply a coolant to the battery 150 to reduce the heat and, in some cases, prevent thermal runaway. The thermal runaway detection and mitigation system 160 may also perform other actions to mitigate risk, e.g., moving the EV 110 to a less populated area in case it catches fire, or instructing people in the EV 110 to leave the EV 110. The thermal runaway detection and mitigation system 160 also communicates with the fleet management system 120 to enable a fleet response, e.g., re-assigning a different EV in the fleet to complete a task assigned to the EV 110. While the thermal runaway detection and mitigation system 160 is shown as a component of the EV 110, in some embodiments, some or all components of the thermal runaway detection and mitigation system 160 are implemented outside of the EV 110, e.g., in the fleet management system 120, at a cloud server, in an EV facility, etc. The thermal runaway detection and mitigation system 160 is described further in relation to FIG. 2.

In some embodiments, the EV 110 includes multiple batteries 150, e.g., a first battery used to power vehicle propulsion, and a second battery used to power AV hardware (e.g., the sensor suite 140 and the onboard computer). In such embodiments, the EV 110 may include multiple thermal runaway detection and mitigation systems (e.g., one for each battery), or some elements of a single thermal runaway and mitigation system may be duplicated for each battery. For example, the thermal runaway detection and mitigation system 160 may include multiple sets of battery sensors, each set associated with a different battery of the EV 110.

The fleet management system 120 manages the fleet of EVs 110. The fleet management system 120 may manage a service that provides or uses the EVs 110, e.g., a service for providing rides to users using the EVs 110, or a service that delivers items using the EVs (e.g., prepared foods, groceries, packages, etc.). The fleet management system 120 may select an EV from a fleet of EVs to perform a particular service or other task, and instruct the selected EV (e.g., EV 110a) to autonomously drive to a particular location (e.g., a delivery address). The fleet management system 120 also manages fleet maintenance tasks, such as charging and servicing of the EVs 110. As shown in FIG. 1, each of the EVs 110 communicates with the fleet management system 120. The EVs 110 and fleet management system 120 may connect over a public network, such as the Internet. The fleet management system 120 is described further in relation to FIG. 3.

Example Thermal Runaway Detection and Mitigation System

Figure 2:
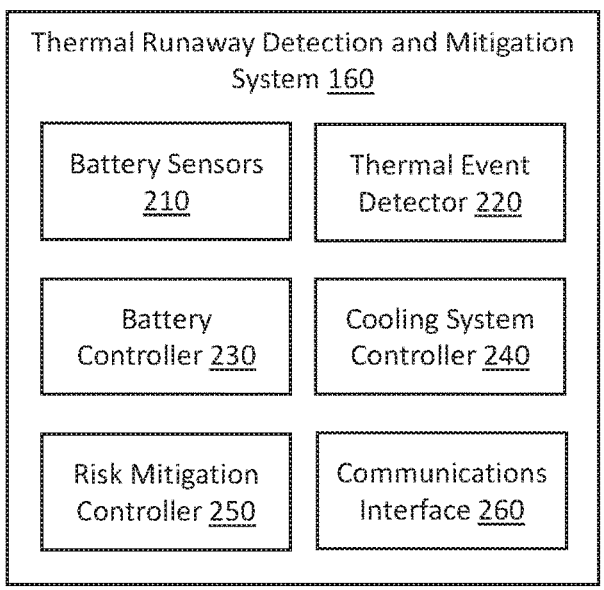
FIG. 2 is a block diagram illustrating a thermal runaway detection and mitigation system according to some embodiments of the present disclosure.

FIG. 2 is a block diagram illustrating the thermal runaway detection and mitigation system 160 according to some embodiments of the present disclosure. The thermal runaway detection and mitigation system 160 includes battery sensors 210, a thermal event detector 220, a battery controller 230, a cooling system controller 240, a risk mitigation controller 250, and a communications interface 260. In alternative configurations, fewer, different and/or additional components may be included in the thermal runaway detection and mitigation system 160. For example, in some configurations, the battery controller 230, cooling system controller 240, and/or communication interface 260 are included in other systems of the EV 110. Further, functionality attributed to one component of the thermal runaway detection and mitigation system 160 may be accomplished by a different component included in the thermal runaway detection and mitigation system 160 or a different system than those illustrated. For example, in some embodiments, some elements of the thermal runaway detection and mitigation system 160 (e.g., the thermal event detector 220 or risk mitigation controller 250) the may be implemented by the fleet management system 120 or by another server or device.

Figure 4:
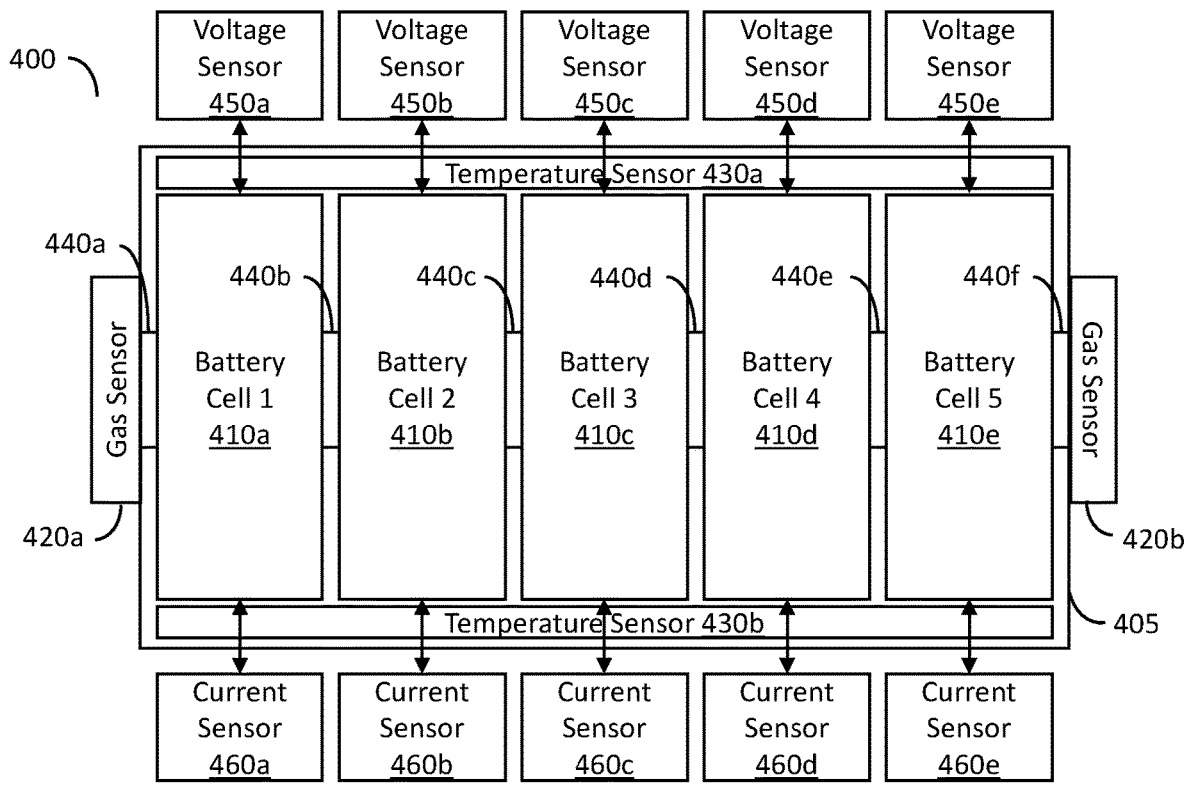
FIG. 4 illustrates an example battery assembly with various battery sensors according to some embodiments of the present disclosure.

The battery sensors 210 measure physical properties of the battery 150 or an area around the battery 150. The battery sensors 210 may include gas sensors, temperature sensors, pressure sensors, current sensors, and/or voltage sensors. The battery sensors 210 may include one type of sensor (e.g., gas sensors) or multiple types of sensors (e.g., both battery sensors and pressure sensors). Multiple battery sensors of a single type may be positioned at different locations around the battery 150 to take measurements associated with different portions of the battery 150. An example set of battery sensors 210 are shown in FIG. 4.

The battery sensors 210 may include one or more gas sensors configured to detect levels of specific types of gasses in the vicinity of the battery 150 that can be used to determine if the battery is out-gassing. For example, a gas sensor may detect concentrations of one or more gasses that are released by an out-gassing battery, e.g., hydrogen, carbon monoxide, carbon dioxide, or hydrocarbons (e.g., $H_2C_4$, $H_2C_6$, etc.). A gas sensor may detect concentrations of typical environmental gasses, e.g., nitrogen and oxygen, which may be present at lower concentrations than usual during an out-gassing event. In some embodiments, different sensors are included to measure concentrations of different types of gasses. The specific gasses that are released during out-gassing depend on the battery technology, and the gas sensors may be selected based on the battery 150. A gas sensor may detect one or more gas ratios, e.g., a ratio of hydrogen to nitrogen, or a ratio of carbon monoxide to oxygen. The gas sensors may be positioned near vents of the battery 150. The gas sensors may be positioned inside or outside the battery 150.

The battery sensors 210 may include pressure sensors configured to measure pressure levels within the battery 150, e.g., between two cells of the battery. The battery sensors 210 may include temperature sensors configured to measure a temperature of the battery. The temperature sensors may also be positioned near vents of the battery 150, or at other positions that heat more quickly during a thermal runaway event. The battery sensors 210 may include voltage sensors that measure a voltage output or received by respective cells of the battery 150. The battery sensors 210 may include current sensors that measure a current output or received by respective cells of the battery 150. In some embodiments, the voltage sensors and/or current sensor measure voltage or current, respectively, applied to the cells during charging, e.g., while the EV 110 is being charged at a charging station, or during regenerative braking.

The thermal event detector 220 receives signals from the battery sensors 210 and determines, based on the signals, whether the battery 150 is experiencing out-gassing. For example, the thermal event detector 220 receives a measured level of at least one type of gas (e.g., hydrogen), and determines that the battery 150 is experiencing out-gassing based on the level of the gas. The thermal event detector 220 may apply one or more thresholds or decision-making rules to the signals received from the battery sensors 210.

In a simple example, the battery sensors 210 include five hydrogen sensors located in different positions around the battery 150. If any of the hydrogen sensors reports a hydrogen concentration above a threshold concentration, the thermal event detector 220 determines that the battery 150 is experiencing out-gassing. In another example, the thermal event detector 220 receives a ratio of a concentration of a first type of gas (e.g., hydrogen) to a second type of gas (e.g., nitrogen), or calculates a ratio between two types of gasses based on two sensor readings. The thermal event detector 220 determines that the battery is experiencing out-gassing in response to a change in the ratio, or the ratio being greater than or lower than a particular threshold.

The thermal event detector 220 may receive signals from multiple types of sensors and identify out-gassing based on a combination of signals. In particular, in addition to the gas sensor signals, the thermal event detector 220 may identify out-gassing based on a pressure level between two cells of the battery 150, a temperature measured in or around the battery 150 (e.g., near a vent of the battery), a current reading of one of the cells of the battery, and/or a voltage reading of one of the cells of the battery. For example, the thermal event detector 220 may determine that the battery 150 is experiencing out-gassing in response to (1) a concentration of hydrogen measured at any gas sensor being above a first threshold concentration; (2) a pressure level between any two cells being above a first threshold pressure; or (3) a concentration of hydrogen being above a second, lower threshold concentration, and a pressure level between any two cells being above a second, lower threshold pressure.

The thermal event detector 220 may apply more complex decision rules. In some embodiments, the thermal event detector 220 is trained using machine learning. For example, a data set of various sensor readings obtained both during normal operation and during out-gassing events can be used to train a neural network that receives signals from the battery sensors 210, applies weights to the signals (the weights having been calculated during training of the neural network), combines the weighted signals, and outputs a signal based on the combination of weighted signals, the output signal indicating whether or not the battery 150 is experiencing out-gassing.

In some embodiments, the thermal event detector 220 monitors the signals from the battery sensors 210 in real time to determine the current battery status and/or predict the trajectory of a potential thermal runaway. For example, the thermal event detector 220 may determine the extent of the out-gassing, e.g., based on real-time concentration measurements of one or more gasses. The thermal event detector 220 may also determine whether thermal runaway has occurred, e.g., based on the measured temperature or other signals. The thermal event detector 220 may predict whether the battery 150 is partially or temporarily operational during or after the out-gassing event, e.g., if thermal runaway has been or can be controlled, or if voltage sensors or current sensors indicate that the battery 150 is providing power to the EV 110.

The battery controller 230 interfaces with the battery 150. The battery controller 230 receives a signal from the thermal event detector 220 indicating a current state of the battery 150, e.g., whether the battery 150 is experiencing out-gassing or thermal runaway. In response to a thermal runaway or potential thermal runaway, the battery controller 230 can stop or reduce power drawn from the battery 150. The battery controller 230 may instruct the battery 150 to enter a low-power or reduced functionality mode, e.g., a mode that enables the EV 110 to travel at a low speed, or a mode that enables the EV 110 to provide alerts to riders, but not to travel.

The cooling system controller 240 controls one or more systems for cooling the battery 150. The battery cooling system may use liquid coolants, air cooling, cooling fins, or other cooling techniques. The cooling system controller 240 may perform battery cooling during normal operation of the EV 110. The cooling system controller 240 receives a signal from the thermal event detector 220 indicating the current state of the battery, e.g., whether the battery 150 is experiencing out-gassing or thermal runaway. In response to a thermal runaway or potential thermal runaway, the cooling system controller 240 may increase the use of the cooling system(s), e.g., by increasing the amount of liquid coolant applied to the battery 150. In addition, the cooling system controller 240 may use one or more back-up cooling methods that are not used during normal operation. For example, the cooling system controller 240 may direct wiper fluid to the battery 150 as an additional coolant.

In some embodiments, the cooling system controller 240 receives multiple signals from the thermal event detector 220 corresponding to different portions of the battery 150, the signals indicating, based on the measurements from different sensors located at different locations around the battery, a particular portion of the battery (e.g., a cell or set of cells) that is experiencing out-gassing. The cooling system controller 240 identifies a portion of the battery based on these signals and directs a liquid stored on the EV 110 (e.g., a battery coolant liquid, or a back-up coolant such as wiper fluid) to the identified portion of the battery. This allows the on-board cooling resources to be deployed to the portion of the battery that most needs to be cooled, and may enable the prevention of thermal runaway using limited on-board resources.

The risk mitigation controller 250 identifies risks associated with thermal runaway, determines actions that may mitigate the identified risks, and implements the actions. In particular, the risk mitigation controller 250 identifies risks to the EV 110, to people or property within the EV 110, and/or to people or property in the environment of the EV 110 that may be impacted by a thermal runaway event or a fire in the EV 110. The risk mitigation controller 250 may identify risks based on data received from the fleet management system 120, e.g., data indicating people or property currently riding in the EV 110 based on a service assignment. The risk mitigation controller 250 may identify risks based on data received from the sensor suite 140, e.g., data describing people, animals, and property in the environment of the EV 110. The risk mitigation controller 250 also receives signals from the thermal event detector 220 and/or battery controller 230 describing a current state of the battery. The risk mitigation controller 250 determines which actions to take based on the state of the battery, e.g., based on the likelihood that thermal runaway will occur and lead to a fire, or based on the ability of the EV 110 to draw power from the battery 150 and move to a different location.

The risk mitigation controller 250 may scan its environment to find an area that it can maneuver to that reduces risks to the EV's surroundings. For example, the risk mitigation controller 250 identifies a person in the environment of the EV 110 and within a threshold distance from the EV 110, e.g., 5 meters or 10 meters. The risk mitigation controller 250 identifies a location in the environment of the EV 110 that is beyond the threshold distance from person, and now within the threshold distance from another person. The risk mitigation controller 250 may identify the person and the location beyond the threshold distance from the person based on data from the sensor suite 140. For example, the risk mitigation controller 250 may identify an empty parking lot or field. The risk mitigation controller 250 instructs the EV 110 to autonomously maneuver to the identified location. In this identified location, the EV 110 has a reduced risk of injuring people if the EV 110 catches fire. Furthermore, if the EV 110 removes itself from a road on which it is traveling, this reduces the risk of injury and/or inconvenience to other traffic in the area.

In another example, the risk mitigation controller 250 determines that a rider is in the EV 110, e.g., based on data describing the EV's current assignment, or based on sensors in the EV 110 for detecting riders. In response to a signal indicating that the battery 150 is experiencing out-gassing, the risk mitigation controller 250 provides an alert, such as an audio alert or a visual alert, to the rider advising the rider to exit the EV 110. In some embodiments, the rider is immediately advised to exit the EV 110 when a potential out-gassing event is identified, even if the cooling system controller 240 may be able to control the out-gassing event to prevent thermal runaway.

The communications interface 260 is configured to communicate with the fleet management system 120. For example, the communications interface 260 is configured to transmit an alert to the fleet management system in response to the thermal event detector determining that the battery is experiencing out-gassing. The communications interface 260 may further provide status updates to the fleet management system 120 with further information from the out-gassing event received from any of the other components of the thermal runaway detection and mitigation system 160. For example, the communications interface 260 may provide updated sensor readings from the battery sensors 210 (e.g., whether gas concentrations have changed, what the current temperature readings are), updates about the current battery status from the battery controller 230 (e.g., whether the battery 150 is operational, operating in a degraded state, or not operating), and updates regarding risk mitigation actions from the risk mitigation controller 250 (e.g., whether the EV 110 has moved to a safer location). The communications interface 260 may provide a current location of the EV 110 to the fleet management system 120.

Example Fleet Management System

Figure 3:
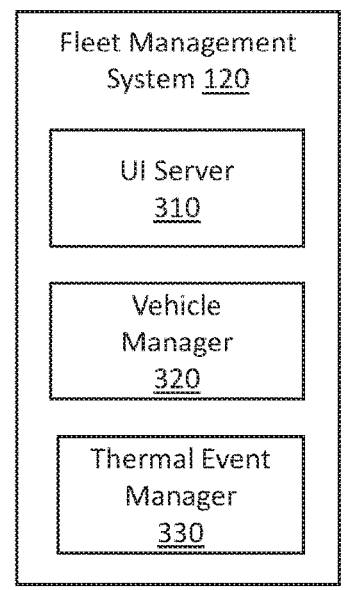
FIG. 3 is a block diagram illustrating a fleet management system according to some embodiments of the present disclosure.

FIG. 3 is a block diagram illustrating the fleet management system 120 according to some embodiments of the present disclosure. The fleet management system 120 includes a UI (user interface) server 310, a vehicle manager 320, and a thermal event manager 330. In alternative configurations, different and/or additional components may be included in the fleet management system 120. Further, functionality attributed to one component of the fleet management system 120 may be accomplished by a different component included in the fleet management system 120 or a different system than those illustrated.

The UI server 310 is configured to communicate with client devices that provide a user interface to users. For example, the UI server 310 may be a web server that provides a browser-based application to client devices, or the UI server 310 may be a mobile app server that interfaces with a mobile app installed on client devices. The user interface enables the user to access a service of the fleet management system 120, e.g., to request a ride from an EV 110, or to request a delivery from an EV 110.

The vehicle manager 320 manages and communicates with a fleet of EVs, including EVs 110a through 110N. The vehicle manager 320 may assign EVs 110 to various tasks and direct the movements of the EVs 110 in the fleet. For example, the vehicle manager 320 assigns an EV 110 to perform a service requested by a user to the UI server 310. The vehicle manager 320 may instruct EVs 110 to drive to other locations while not servicing a user, e.g., to improve geographic distribution of the fleet, to anticipate demand at particular locations, etc. The vehicle manager 320 also instructs EVs 110 to return to EV facilities for recharging, maintenance, or storage.

The thermal event manager 330 communicates with an EV 110 experiencing out-gassing and manages a real-time response to thermal runaway or out-gassing. The thermal event manager 330 receives the alerts and status updates from the communications interface 260 described above with respect to FIG. 2. The thermal event manager 330 alters an assignment of the EV 110 experiencing out-gassing, e.g., redirecting the EV 110 from its current assignment, or re-assigning the task to another EV 110. The thermal event manager 330 provides instructions to the EV 110 experiencing out-gassing, e.g., to move to a different location, to return to an EV facility, or to stay in place and await assistance.

In one embodiment, the thermal event manager 330 receives a status update from the communications interface 260 of the EV 110, e.g., a status update describing a current state of the battery, or indicating that the cooling system has suppressed the thermal event. Based on the status update, the thermal event manager 330 determines that the EV 110 can safely travel to an EV facility. This determination may also be based on the proximity of the EV 110 to the EV facility, e.g., the EV 110 is able to travel to the EV facility with a battery in a degraded state that can only power the EV 110 at low speeds or for short distances. The thermal event manager 330 transmits instructions to the EV 110 to autonomously maneuver to the EV facility for servicing the battery 150, thus altering the assignment of the EV 110. The instructions may include particulars of the route, e.g., to travel on surface roads, or to travel on less trafficked roads.

In another embodiment, the thermal event manager 330 requests an emergency response for the EV 110. For example, if the thermal event manager 330 receives a status update from the EV 110 indicating that the battery 150 is experiencing unrestrained thermal runaway, and receives a current location of the EV 110. The thermal event manager 330 transmits a message to an emergency services provider requesting an emergency response to the EV 110. The message includes the current location of the EV 110 so that a first responder can locate the EV 110. The message may include additional information about the EV 110, such as whether riders were in the EV 110 when the thermal runaway event occurred. The thermal event manager 330 may transmit the message to a public emergency services provider (e.g., a 911 call center), or to a private emergency services provider. In some embodiments, the EV 110 (e.g., the communications interface 260 and the risk mitigation controller 250) contact an emergency services provider directly.

In another embodiment, the thermal event manager 330 (or the vehicle manager 320) alters the assignment of the EV 110 by assigning another EV in the fleet to complete the assignment. In particular, the thermal event manager 330 identifies a second EV in the fleet managed by the fleet management system 120 (e.g., the fleet of EVs 110) that is available to complete the assignment of the EV 110, and transmits instructions to the second EV to complete the assignment of the EV 110. For example, if the EV 110 was previously tasked to pick up an item and deliver it to a particular address, the thermal event manager 330 instructs the second EV to pick up the item (either from the pick-up location, or from the EV 110) and deliver it to the address. If the EV 110 was giving a ride to a user, the thermal event manager 330 instructs the second EV to travel to the location of the EV 110 and to pick up the user to continue the user's ride. The thermal event manager 330 may alter the assignment based on the out-gassing event. For example, if the user was injured in a fire, the thermal event manager 330 may instruct the second EV to pick up the user and transport the user to a hospital, rather than the user's original destination.

Example Battery with Sensors

FIG. 4 illustrates an example battery assembly with various battery sensors according to some embodiments of the present disclosure. The battery assembly 400 has a set of battery cells 410 arranged alongside each other within a battery case 405. In this example, the battery assembly 400 has five battery cells: cell 1 410a, cell 2 410b, cell 3 410c, cell 4 410d, and cell 5 410e. In other embodiments, the battery assembly 400 may have fewer or more cells 410, and the battery cells may have different arrangements.

The battery assembly 400 includes a set of sensors 420-450, which include gas sensors 420a and 420b, temperature sensors 430a and 430b, pressure sensors 440a-440f, voltage sensors 450a-450e, and current sensors 460a-460e. The gas sensors 420a and 420b are mounted outside the battery case 405. The gas sensors 420a and 420b may be mounted near vents in the battery case 405. The temperature sensors 430a and 430b are located within the battery case 405. The temperature sensors 430a and 430b are shown running along the length of the battery assembly 400. The temperature sensors 430a and 430b may each be an assembly of multiple sensors, e.g., an assembly of five sensors, with one sensor in the assembly located proximate to a respective battery cell 410. The numbers and arrangements of the temperature sensors 430 and gas sensors 420 can be different in other embodiments; for example, each may be inside or outside the battery case 405, located in different positions relative to the battery cells 410, and more or less of each type of sensor may be included.

The first pressure sensor 440a and sixth pressure sensor 440f are positioned between battery cells (battery cell 1 410a and battery cell 5 410e, respectively) and the battery case 405 to measure a pressure exerted by the battery cells 410a and 410e in the direction of the battery case 405. The second through fifth pressure sensors, 440b, 440c, 440d, and 440e, are each located between two battery cells 410. These pressure sensors 440b-440e measure pressure exerted by the battery cells 410 against other battery cells. For example, the third pressure sensor 440c measures pressure between battery cell 2 410b and battery cell 3 410c, e.g., pressure exerted by battery cell 2 410b in the direction of battery cell 3 410c, or pressure exerted by battery cell 3 410c in the direction of battery cell 2 410b. During an out-gassing event, the pressure within a battery cell 410 that is out-gassing increases, which can be measured via the pressure sensors 440. In other embodiments, more or fewer pressure sensors 440 may be included, or pressure sensors may be arranged differently. For example, pressure sensors 440 may be included at the ends of the battery cells 410, e.g., where the temperature sensors 430 are located in FIG. 4.

Each battery cell 410 is connected to a corresponding voltage sensor 450 and current sensor 460. The voltage sensors 450 measure voltages output by or received by the battery cells 410, e.g., voltage sensor 450a measures a voltage output by the first battery cell 410a during operation of the EV 110, or voltage sensor 450a measures a voltage received by the first battery cell 410a during charging of the battery. The current sensors 460 measure currents output by or received by the battery cells 410, e.g., current sensor 460a measures a current output by the first battery cell 410a during operation of the EV 110, or current sensor 460a measures a current received by the first battery cell 410a during charging of the battery. While the voltage sensors 450 and current sensors 460 are depicted on opposite sides of each battery cell 410, in some embodiments, the voltage sensor 450 and current sensor 460 share a connection point to a battery cell 410, and may be integrated into a single current and voltage measuring device. For example, the voltage sensors 450 and current sensors 460 may be part of the power system of the EV 110, and signals are sent from the power system to the thermal event detector 220.

Example Process for On-Board Thermal Runaway Detection and Mitigation

Figure 5:
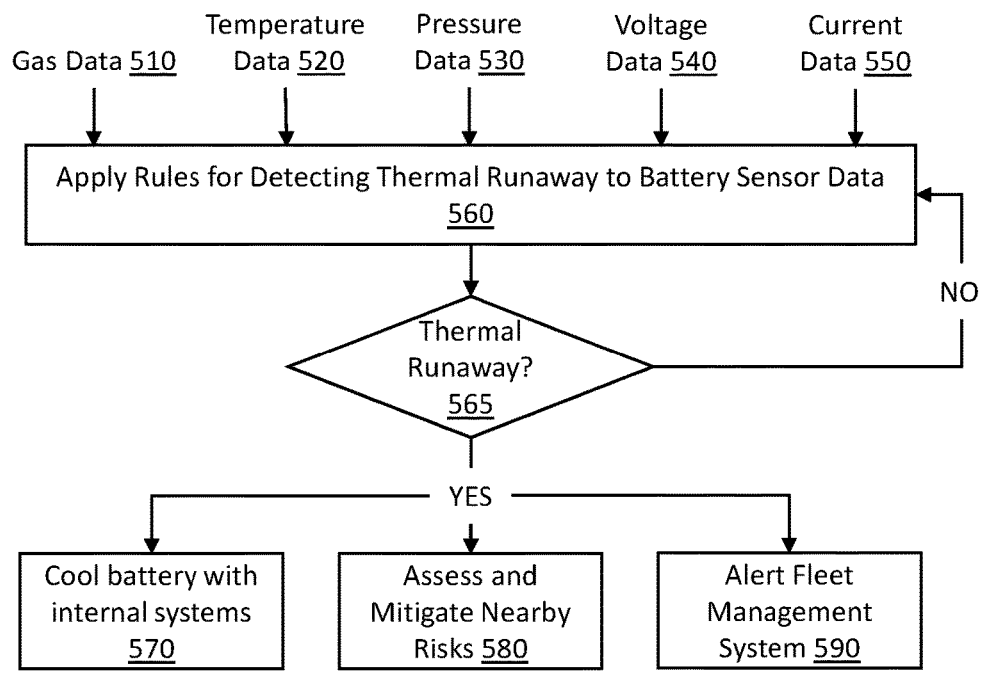
FIG. 5 is a flowchart showing a process for on-board detecting and mitigating thermal runaway according to some embodiments of the present disclosure.

FIG. 5 is a flowchart showing a process for on-board detecting and mitigating thermal runaway according to some embodiments of the present disclosure. In this example, a battery assembly, such as battery assembly 400 shown in FIG. 4, has battery sensors including gas sensors (e.g., gas sensors 420), temperature sensors (e.g., temperature sensors 430), pressure sensors (e.g., pressure sensors 440), voltage sensors (e.g., voltage sensors 450), and current sensors (e.g., current sensors 460). The battery sensors provide gas data 510, temperature data 520, pressure data 530, voltage data 540, and current data 550 to a thermal event detector, e.g., thermal event detector 220. The thermal event detector applies 560 rules for detecting thermal runaway to the battery sensor data 510-550. For example, the thermal event detector applies rules to process the battery sensor data 510-550 as described above with respect to FIG. 2. In some embodiments, only a portion of the data 510-550 shown in FIG. 5 is provided to the thermal event detector, e.g., voltage data 540 may not be provided if the battery assembly does not include voltage sensors 450.

The thermal event detector determines 565 whether thermal runaway is occurring or likely to occur based on the application of the rules. If the thermal event detector does not detect a potential thermal runaway event, the thermal event detector continues applying 560 the rules based on new data 510-550 received from the battery sensors. If the thermal event detector does detect a potential thermal runaway event, the thermal event detector transmits a signal to other components of the EV 110 to mitigate the risks. In particular, the EV 110 (e.g., cooling system controller 240) cools 570 the battery with internal cooling systems, e.g., an on-board battery coolant, or one or more back-up cooling materials. The EV 110 also (e.g., a risk mitigation controller 250) assesses and mitigates 580 nearby risks, e.g., risks to humans nearby or in the EV 110, or risks to property. The EV 110 (e.g., a communications interface 260) alerts 590 a fleet management system 120, e.g., the thermal event manager 330, which coordinates a fleet response to the thermal event. In particular, the fleet management system 120 alters an assignment of the EV 110 in response to the out-gassing of the battery, e.g., removing the EV 110 from its assignment and/or assigning a different EV to complete the assignment.

Example EV Facility-Based Thermal Event Detection and Mitigation System

In another embodiment, a system for detecting, suppressing, and mitigating a thermal runaway event is implemented within an EV facility, such as a facility for charging, storing, or performing maintenance on EVs. Some EV batteries are at particular risk of thermal runaway when they are being charged. A facility-based system can receive signals from sensors mounted in the EV facility and any on-board sensors, such as the sensors shown in FIG. 4. The facility-based system processes the sensor data to determine whether out-gassing and/or thermal runaway is occurring, if so, and takes actions to protect the EV, the facility, nearby EVs, and any people within the EV facility.

A thermal runaway detection and mitigation system similar to the thermal runaway detection and mitigation system 160, described with respect to FIGS. 1 and 2, may be included within the EV facility and/or at the fleet management system 120 to detect and respond to thermal runaway events. For example, battery sensors 210 and/or in-facility sensors (e.g., gas sensors mounted within the EV facility) transmit sensor data to a thermal runaway detection and mitigation system implemented by the fleet management system 120, e.g., by the thermal event manager 330. In this example, the fleet management system 120 implements the thermal event detector 220, cooling system controller 240, and risk mitigation controller 250. The thermal event manager 330 may be implemented by a computer located on-site at the EV facility or at a cloud-based server.

Figure 6:
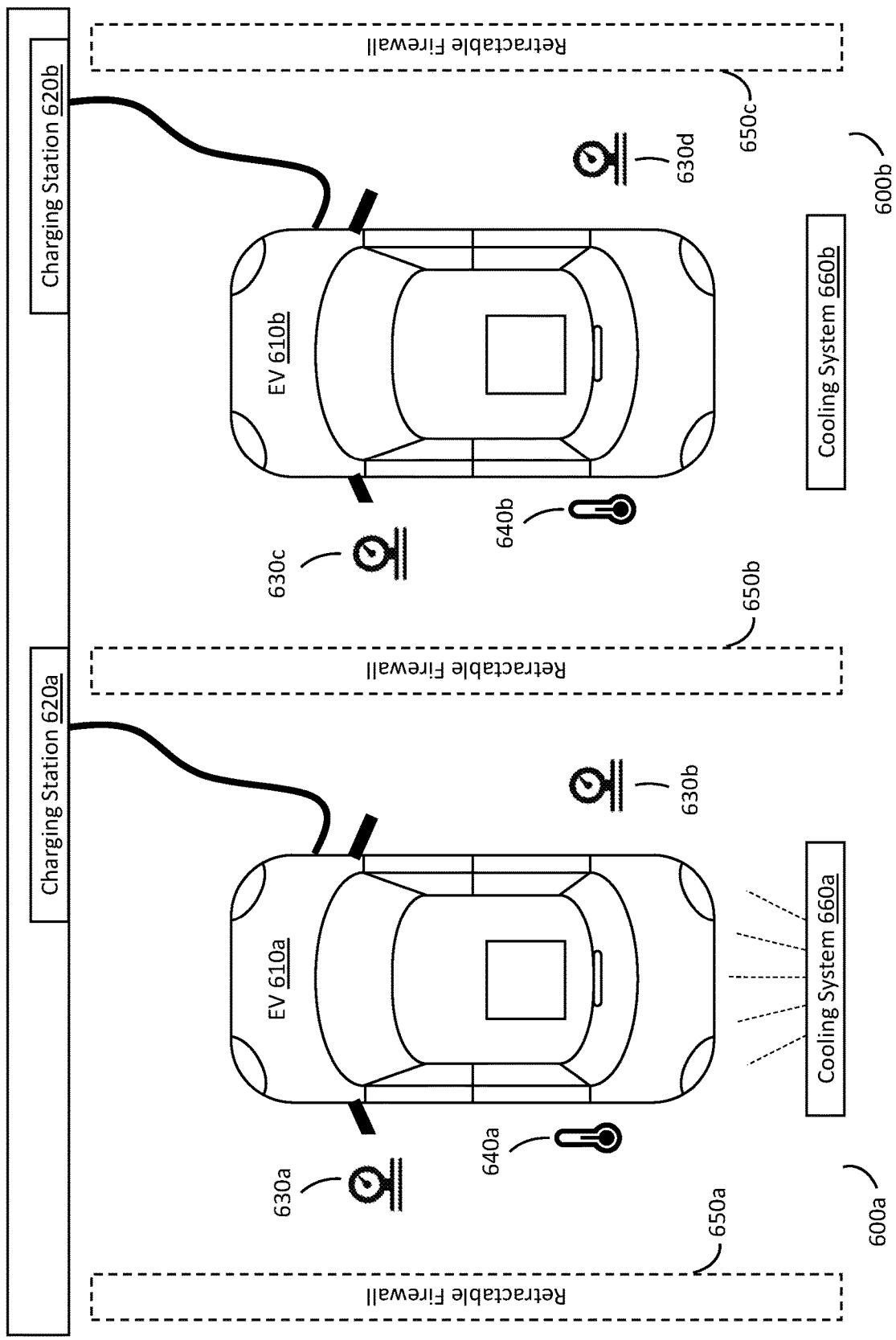
FIG. 6 illustrates an example use case of two EVs within an EV facility with a system for detecting and suppressing thermal runaway according to some embodiments of the present disclosure.

FIG. 6 illustrates an example use case of two EVs, 610a and 610b, within an EV facility that has a system for detecting and suppressing thermal runaway according to some embodiments of the present disclosure. In this example, the EV facility includes spots 600 for EVs, two of which are shown in FIG. 6. The EV facility may have more or fewer spots 600, e.g., the two spots 600a and 600b in FIG. 6 may be a portion of a longer row of similar spots. Each spot 600 has a respective charging station 620 for charging an EV 610 parked in the spot. For example, charging station 620a has a cord connecting to EV 610a to charge the EV 610a. The charging station 620a may include a voltage sensor that measures the voltage of a charge provided from the charging station 620a to the EV 610a. The charging station 620a may also have a current sensor, power sensor, or one or more additional or alternative sensors for monitoring the charge being delivered to the EV 610a and/or amount of energy transferred to the EV 610a by the charging station 620a. A disruption to the flow of energy from a charging station 620 to an EV 610 can indicate that the battery of the EV 610 is malfunctioning, e.g., is experiencing out-gassing or thermal runaway.

The EV facility also includes various sensors, such as gas sensors 630 and temperature sensors 640, located around the EVs 610 in the spots 600. For example, two gas sensors 630a and 630b and one temperature sensor 640a are located near EV 610a, and two gas sensors 630c and 640d and one temperature sensor 640b are located near EV 610b. Additional or fewer sensors may be included, and the locations of the sensors may differ from the locations shown in FIG. 6. For example, one or more sensors may be located underneath each EV 610 and closer to the battery. More particularly, if the batteries of the EVs 610 have vents on their undersides, gas and/or temperature sensors may be arranged directly underneath the vents when the EVs 610 are parked in particular positions within the spots 600. The EV facility may have guide posts (e.g., markings on the walls or floor) that the EVs 610 can when parking so that the EVs 610 are aligned with the sensors.

A thermal runaway detection and mitigation system receives readings from the charging stations 620, gas sensors 630, and temperature sensors 640. The thermal runaway detection and mitigation system may also receive sensor readings from any sensors located on-board the EVs 610, e.g., any of the sensors shown in FIG. 4. The thermal runaway detection and mitigation system processes the sensor readings to determine whether a battery of an EV 610 is experiencing out-gassing or thermal runaway. The thermal runaway detection and mitigation system may use a thermal event detector similar to the thermal event detector 220 describe with respect to FIG. 2. For example, the thermal event detector applies a set of thresholds, or uses a machine-learned model, to analyze the sensor data from the charging station 620 and sensors 630 and 640, and to determine based on the sensor data if the battery of the EV 610 is experiencing out-gassing.

The EV facility can be built to include fire suppression and mitigation equipment. For example, FIG. 6 includes two cooling system 660a and 660b, one corresponding to each EV 610. The cooling systems 660 are configured to apply a coolant to an EV 610 that is experiencing out-gassing; for example, cooling system 660a is shown spraying a coolant (e.g., cold water or another substance) onto the EV 610a, and in particular, onto the underside of EV 610a, where the battery is located. More or fewer cooling systems 660 may be included, e.g., one cooling system may be configured to spray coolant onto multiple EVs. The cooling systems 660 may be arranged differently than shown in FIG. 6, e.g., a cooling system 660 may be located directly underneath each EV 610.

FIG. 6 also includes retractable firewalls 650a, 650b, and 650c. Each spot 600 within the EV facility may be able to be bounded on one or more sides by retractable firewalls 650 that can block neighboring EVs from a battery fire of an EV that is out-gassing. The retractable firewalls 650 may be stored in the floor, ceiling, or within fixed walls during normal operation of the EV facility. The firewalls 650 deployed in response to the thermal runaway detection and mitigation system detecting out-gassing. Alternatively, the EV facility may have fixed firewalls between neighboring EV spots. Using retractable firewalls 650 may allow for less space between adjacent EVs (e.g., less space is needed to allow doors to open and close) and increased visibility across the EV facility than if fixed firewalls are built between each spot.

Example Process for EV Facility Thermal Runaway Detection and Mitigation

Figure 7:
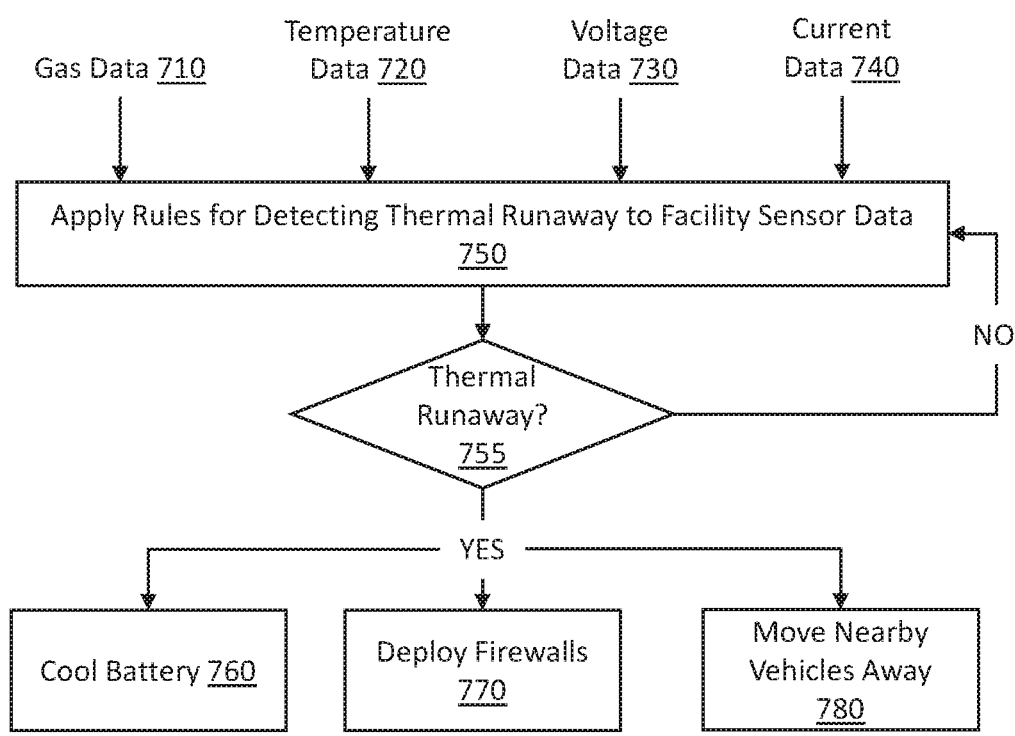
FIG. 7 is a flowchart showing a process for detecting and mitigating thermal runaway within an EV facility according to some embodiments of the present disclosure.

FIG. 7 is a flowchart showing a process for detecting and mitigating thermal runaway for an EV within an EV facility according to some embodiments of the present disclosure. In this example, the EV facility sensors, namely the gas sensors 630 and temperature sensors 640 near the EV, and the voltage sensors and current sensors in the charging stations 620, provide gas data 710, temperature data 720, voltage data 730, and current data 740 to a thermal event detector, e.g., thermal event detector 220. The thermal event detector applies 750 rules for detecting thermal runaway to the facility sensor data 710-740. In some embodiments, the thermal event detector may consider data from more or fewer sensors, e.g., the thermal event detector may also receive data from battery sensors such as those shown in FIG. 4.

The thermal event detector determines 755 whether a battery of an EV 610 within the EV facility is experiencing out-gassing, indicating that thermal runaway is occurring or likely to occur, based on the application of the rules. If the thermal event detector does not detect a potential thermal runaway event, the thermal event detector continues applying 750 the rules based on new data 710-740 from the EV facility sensors. If the thermal event detector does detect a potential thermal runaway event, the thermal event detector alerts the fleet management system 120, which coordinates a fleet response. In particular, the fleet management system 120 identifies any other EVs within range of the EV 610 experiencing out-gassing, and instructs an action to the EV facility and/or the identified EV to protect the EV from potential fire damage.

For example, the thermal event detector determines that the EV 610a is experiencing out-gassing and is at risk for thermal runaway. The fleet management system 120 identifies that EV 610b is within a threshold range (e.g., parked in an adjacent spot, or within 10 meters of EV 610a). The fleet management system 120 may instruct the cooling system 660a to cool 760 the battery of the EV 610a, e.g., by spray watering onto EV 610a, to prevent a fire. The fleet management system 120 may also instruct the cooling system 660b to spray water onto EV 610b to reduce the heat and fire risk to EV 610b. The fleet management system 120 may instruct the retractable firewall 650b to deploy 770, to protect EV 610b from a potential battery fire. In addition, or alternatively, the fleet management system 120 may instruct the EV 610b to move away 780 from EV 610a. For example, the fleet management system 120 may instruct the EV 610b to autonomously maneuver to a different spot within the EV facility, or to exit the EV facility.

SELECT EXAMPLES

Example 1 provides a system for mitigating thermal runaway in a battery-powered electric vehicle (EV) including a gas sensor, a thermal event detector, and a communications interface. The gas sensor is configured to measure a level of at least one type of gas in a vicinity of a battery of the EV. The thermal event detector is configured to determine, based on the measured level of the at least one type of gas, that the battery is experiencing out-gassing. The communications interface is configured to transmit an alert to a fleet management system regarding the out-gassing of the battery. The fleet management system is configured to alter an assignment of the EV in response to the out-gassing of the battery.

Example 2 provides the system according to example 1, where the gas sensor is configured to measure a concentration of hydrogen in the vicinity of the battery of the EV, and the thermal event detector is configured to determine that the battery is experiencing out-gassing in response to the concentration of hydrogen being greater than a threshold concentration.

Example 3 provides the system according to example 1 or 2, where the gas sensor is configured to measure a first concentration of a first type of gas and a second concentration of a second type of gas in the vicinity of the battery of the EV, and the thermal event detector is configured to determine that the battery is experiencing out-gassing in response to a change in a ratio of the first concentration to the second concentration.

Example 4 provides the system according to any of the preceding examples, where the battery of the EV includes a plurality of cells, the system further includes a pressure sensor configured to measure a pressure level between two cells of the battery, and the thermal event detector is configured to determine that the battery is experiencing out-gassing further based on the measured pressure level between the two cells.

Example 5 provides the system according to any of the preceding examples, where the system further includes a temperature sensor configured to measure a temperature of the battery, and the thermal event detector is configured to determine that the battery is experiencing out-gassing further based on the measured temperature of the battery.

Example 6 provides the system according to any of the preceding examples, where the battery of the EV includes a plurality of cells, the system further includes a plurality of voltage sensors each configured to measure a voltage output by a respective cell of the battery or current sensors each configured to measure a current output by a respective cell of the battery, and the thermal event detector is configured to determine that the battery is experiencing out-gassing further based on at least one of the measured voltages or currents.

Example 7 provides the system according to any of the preceding examples, where a cooling system is configured to apply a coolant stored on the EV to the battery in response to the determination by the thermal event detector that the battery is experiencing out-gassing.

Example 8 provides the system according to any of the preceding examples, where altering the assignment of the EV includes receiving at least one status update transmitted by the communications interface of the EV; determining, based on the status update, that the EV can safely travel to an EV facility; and transmitting instructions to the EV to autonomously maneuver to the EV facility for servicing the battery.

Example 9 provides the system according to any of the preceding examples, where altering the assignment of the EV includes identifying a second EV in a fleet of EVs managed by the fleet management system, the second EV available to complete the assignment of the EV; and transmitting instructions to the second EV to complete the assignment of the EV.

Example 10 provides the system according to any of the preceding examples, where the system further includes a risk mitigation controller configured to identify a person in an environment of the EV, the person within a threshold distance from the EV; identify a location in the environment of the EV beyond the threshold distance from the person; and instruct the EV to autonomously maneuver to the identified location.

Example 11 provides the system according to any of the preceding examples, where the fleet management system is configured to receive a current location of the EV transmitted by the communications interface of the EV, and transmit a message to an emergency services provider, the message requesting an emergency response to the EV and the message including the current location of the EV.

Example 12 provides the system according to any of the preceding examples, where the system further includes a risk mitigation controller configured to determine that a rider is in the EV, and provide at least one of an audio alert and a visual alert to the rider advising the rider to exit the EV.

Example 13 provides the system according to any of the preceding examples, where the system further includes a plurality of sensors arranged in different locations around the battery of the EV and configured to obtain measurements associated with different portions of the battery, and a cooling system controller is configured to identify a portion of the battery experiencing out-gassing based on the measurements from the plurality of sensors, and direct a liquid stored on the EV to the identified portion of the battery to cool the identified portion of the battery.

Example 14 provides method for mitigating thermal runaway in a battery-powered electric vehicle (EV) including measuring a level of a type of gas in a vicinity of a battery of the EV; determining, based on the measured level of the type of gas, that the battery is experiencing out-gassing; transmitting an alert to a fleet management system indicating that the battery is experiencing out-gassing; and altering, by the fleet management system, an assignment of the EV in response to the alert.

Example 15 provides the method according to example 14, where the measured level of the type of gas is a first level of a first type of gas, and the method further includes measuring a second level of a second type of gas in the vicinity of the battery of the EV, and comparing the first level of the first type of gas to the second level of the second type of gas to determine that the battery is experiencing out-gassing.

Example 16 provides the method according to example 14 or 15, where the method further includes measuring one of a pressure level between two cells of the battery, a temperature of the battery, and a voltage output by a cell of the battery; and determining that the battery is experiencing out-gassing further based on the one of the pressure level, the temperature, and the voltage.

Example 17 provides the method according to any of examples 14 through 16, where the method further includes directing a coolant stored on-board the EV to the battery in response to the determination that the battery is experiencing out-gassing.

Example 18 provides the method according to any of examples 14 through 17, where altering the assignment of the EV includes receiving at least one status update transmitted to the fleet management system by the EV; determining, based on the status update, that the EV can safely travel to an EV facility; and transmitting instructions to the EV to autonomously maneuver to a facility for servicing the battery.

Example 19 provides the method according to any of examples 14 through 18, where altering the assignment of the EV includes identifying a second EV in a fleet of EVs managed by the fleet management system, the second EV available to complete the assignment of the EV; and transmitting instructions to the second EV to complete the assignment of the EV.

Example 20 provides a system for suppressing thermal runaway in a battery-powered electric vehicle (EV) including a gas sensor configured to measure a level of at least one type of gas in a vicinity of a battery of the EV; a thermal event detector configured to determine, based on the measured level of the at least one type of gas, that the battery is experiencing out-gassing; a cooling system configured to apply a coolant stored on the EV to the battery in response to the determination by the thermal event detector that the battery is experiencing out-gassing; and a communications interface configured to transmit an alert to a fleet management system regarding the out-gassing of the battery.

Example 21 provides a system for suppressing thermal runaway in an electric vehicle (EV) facility including a gas sensor configured to measure a level of at least one type of gas in a vicinity of an EV located at the EV facility; a thermal event detector configured to determine, based on the measured level of the at least one type of gas, that a battery of the EV is experiencing out-gassing; and a fleet management system configured to identify at least one other EV within a threshold range of the EV, and, in response to the determination that the battery is experiencing out-gassing, instruct an action to protect the at least one other EV from fire damage from the battery that is experiencing out-gassing.

Example 22 provides the system according to example 21, where the system further includes a cooling system configured to direct a coolant to the battery that is experiencing out-gassing in response to the determination that the battery is experiencing out-gassing.

Example 23 provides the system according to example 21 or 22, where the system further includes a retractable firewall located between the EV and a second EV, and the action to protect the at least one other EV from fire damage includes deploying the retractable firewall between the EV and the second EV.

Example 24 provides the system according to example 21, 22, or 23, where the action to protect the at least one other EV from fire damage includes instructing the at least one other EV to autonomously maneuver away from the EV.

Example 25 provides a method for suppressing thermal runaway in an electric vehicle (EV) facility including measuring, by a gas sensor, a level of at least one type of gas in a vicinity of an EV located at the EV facility; determining, based on the measured level of the at least one type of gas, that a battery of the EV is experiencing out-gassing; identifying at least on other EV within a threshold range of the EV; and in response to the determination that the battery is experiencing out-gassing, instructing an action to protect the at least one other EV from fire damage from the battery that is experiencing out-gassing.

Example 26 provides the method according to example 25, where the method further includes directing a coolant to the battery that is experiencing out-gassing in response to the determination that the battery is experiencing out-gassing.

Example 27 provides the method according to example 25 or 26, where the action to protect the at least one other EV from fire damage includes deploying a retractable firewall between the EV and the second EV.

Example 28 provides the method according to example 25, 26, or 27, where the action to protect the at least one other EV from fire damage includes instructing the at least one other EV to autonomously maneuver away from the EV.

OTHER IMPLEMENTATION NOTES, VARIATIONS, AND APPLICATIONS

It is to be understood that not necessarily all objects or advantages may be achieved in accordance with any particular embodiment described herein. Thus, for example, those skilled in the art will recognize that certain embodiments may be configured to operate in a manner that achieves or optimizes one advantage or group of advantages as taught herein without necessarily achieving other objects or advantages as may be taught or suggested herein.

In one example embodiment, any number of electrical circuits of the figures may be implemented on a board of an associated electronic device. The board can be a general circuit board that can hold various components of the internal electronic system of the electronic device and, further, provide connectors for other peripherals. More specifically, the board can provide the electrical connections by which the other components of the system can communicate electrically. Any suitable processors (inclusive of digital signal processors, microprocessors, supporting chipsets, etc.), computer-readable non-transitory memory elements, etc. can be suitably coupled to the board based on particular configuration needs, processing demands, computer designs, etc. Other components such as external storage, additional sensors, controllers for audio/video display, and peripheral devices may be attached to the board as plug-in cards, via cables, or integrated into the board itself. In various embodiments, the functionalities described herein may be implemented in emulation form as software or firmware running within one or more configurable (e.g., programmable) elements arranged in a structure that supports these functions. The software or firmware providing the emulation may be provided on non-transitory computer-readable storage medium comprising instructions to allow a processor to carry out those functionalities.

It is also imperative to note that all of the specifications, dimensions, and relationships outlined herein (e.g., the number of processors, logic operations, etc.) have only been offered for purposes of example and teaching only. Such information may be varied considerably without departing from the spirit of the present disclosure, or the scope of the appended claims. The specifications apply only to one non-limiting example and, accordingly, they should be construed as such. In the foregoing description, example embodiments have been described with reference to particular arrangements of components. Various modifications and changes may be made to such embodiments without departing from the scope of the appended claims. The description and drawings are, accordingly, to be regarded in an illustrative rather than in a restrictive sense.

Note that with the numerous examples provided herein, interaction may be described in terms of two, three, four, or more components. However, this has been done for purposes of clarity and example only. It should be appreciated that the system can be consolidated in any suitable manner. Along similar design alternatives, any of the illustrated components, modules, and elements of the FIGS. may be combined in various possible configurations, all of which are clearly within the broad scope of this Specification.

Note that in this Specification, references to various features (e.g., elements, structures, modules, components, steps, operations, characteristics, etc.) included in "one embodiment", "example embodiment", "an embodiment", "another embodiment", "some embodiments", "various embodiments", "other embodiments", "alternative embodiment", and the like are intended to mean that any such features are included in one or more embodiments of the present disclosure, but may or may not necessarily be combined in the same embodiments.

Numerous other changes, substitutions, variations, alterations, and modifications may be ascertained to one skilled in the art and it is intended that the present disclosure encompass all such changes, substitutions, variations, alterations, and modifications as falling within the scope of the appended claims. Note that all optional features of the systems and methods described above may also be implemented with respect to the methods or systems described herein and specifics in the examples may be used anywhere in one or more embodiments.

In order to assist the United States Patent and Trademark Office (USPTO) and, additionally, any readers of any patent issued on this application in interpreting the claims appended hereto, Applicant wishes to note that the Applicant: (a) does not intend any of the appended claims to invoke paragraph (f) of 35 U.S.C. Section 112 as it exists on the date of the filing hereof unless the words "means for" or "step for" are specifically used in the particular claims; and (b) does not intend, by any statement in the Specification, to limit this disclosure in any way that is not otherwise reflected in the appended claims.

What is claimed is:

1. A system for mitigating thermal runaway in a battery-powered electric vehicle (EV) comprising:
    a plurality of sensors arranged in different locations around a battery of the EV and configured to obtain measurements associated with different portions of the battery, the plurality of sensors comprising a gas sensor configured to measure a level of at least one type of gas in a vicinity of the battery of the EV;
    a thermal event detector configured to determine, based on the measured level of the at least one type of gas, that the battery is experiencing a thermal event;
    a communications interface configured to:
        transmit, at a first time, an alert to a fleet management system regarding the thermal event, the fleet management system configured to alter an assignment of the EV in response to the thermal event;
    a cooling system configured to:
        identify a portion of the battery experiencing the thermal event based on the measurements from the plurality of sensors; and
        direct a liquid stored on the EV to the identified portion of the battery to cool the identified portion of the battery;
    the communications interface further configured to:
        transmit, at a second time, an update to the fleet management system, the update indicating that the thermal event has been suppressed, and
        receive, from the fleet management system in response to the update, instructions to autonomously maneuver the EV from a current location to a second location.

2. The system of claim 1, wherein the gas sensor is configured to measure a concentration of hydrogen in the vicinity of the battery of the EV, and the thermal event detector is configured to determine that the battery is experiencing out-gassing in response to the concentration of hydrogen being greater than a threshold concentration.

3. The system of claim 1, wherein the gas sensor is configured to measure a first concentration of a first type of gas and a second concentration of a second type of gas in the vicinity of the battery of the EV, and the thermal event detector is configured to determine that the battery is experiencing out-gassing in response to a change in a ratio of the first concentration to the second concentration.

4. The system of claim 1, wherein the battery of the EV comprises a plurality of cells, the plurality of sensors further comprising a pressure sensor configured to measure a pressure level between two cells of the battery, wherein the thermal event detector is configured to determine that the battery is experiencing the thermal event further based on the measured pressure level between the two cells.

5. The system of claim 1, the plurality of sensors further comprising a temperature sensor configured to measure a temperature of the battery, wherein the thermal event detector is configured to determine that the battery is experiencing the thermal event further based on the measured temperature of the battery.

6. The system of claim 1, wherein the battery of the EV comprises a plurality of cells, the plurality of sensors further comprising a plurality of voltage sensors each configured to measure a voltage output by a respective cell of the battery, wherein the thermal event detector is configured to determine that the battery is experiencing the thermal event further based on at least one of the measured voltages.

7. The system of claim 1, wherein the battery of the EV comprises a plurality of cells, the plurality of sensors further comprising a plurality of current sensors each configured to measure a current output by a respective cell of the battery, wherein the thermal event detector is configured to determine that the battery is experiencing the thermal event further based on at least one of the measured currents.

8. The system of claim 1, wherein the second location is a location of an EV facility for servicing the battery.

9. The system of claim 1, wherein the update comprises at least one updated sensor reading from one of the plurality of sensors.

10. The system of claim 1, wherein altering the assignment of the EV comprises:
identifying a second EV in a fleet of EVs managed by the fleet management system, the second EV available to complete the assignment of the EV; and
transmitting instructions to the second EV to complete the assignment of the EV.

11. The system of claim 1, further comprising a risk mitigation controller configured to:
identify a person in an environment of the EV, the person within a threshold distance from the EV;
identify a location in the environment of the EV beyond the threshold distance from the person; and
instruct the EV to autonomously maneuver to the identified location.

12. The system of claim 1, wherein the fleet management system is configured to:
receive the current location of the EV transmitted by the communications interface of the EV; and
transmit a message to an emergency services provider, the message requesting an emergency response to the EV and the message comprising the current location of the EV.

13. The system of claim 1, further comprising a risk mitigation controller configured to:
determine that a rider is in the EV; and
provide at least one of an audio alert and a visual alert to the rider advising the rider to exit the EV.

14. The system of claim 1, wherein the update comprises an operational status of the battery.

15. The system of claim 1, wherein the update comprises the current location of the EV at the second time, wherein the current location of the EV is different from a location of the EV at the first time.

16. A method for mitigating thermal runaway in a battery-powered electric vehicle (EV) comprising:
obtaining measurements from a plurality of sensors arranged in different locations around a battery of the EV, the measurements associated with different portions of the battery, the measurements including a level of a type of gas in a vicinity of the battery of the EV;
determining, based on the measured level of the type of gas, that the battery is experiencing a thermal event;
identifying a portion of the battery experiencing the thermal event based on the measurements from the plurality of sensors;
directing a liquid stored on the EV to the identified portion of the battery to cool the identified portion of the battery;
transmitting, at a first time, an alert to a fleet management system indicating that the battery is experiencing the thermal event;
transmitting, at a second time, an update to the fleet management system, the update indicating that the thermal event has been suppressed; and
receiving, from the fleet management system in response to the update, instructions to autonomously maneuver the EV from a current location to a second location.

17. The method of claim 16, further comprising measuring one of a pressure level between two cells of the battery, a temperature of the battery, a current output by a cell of the battery, and a voltage output by a cell of the battery, and determining that the battery is experiencing the thermal event further based on the one of the pressure level, the temperature, the current, and the voltage.

18. The method of claim 16, further comprising:
identifying, by the fleet management system, a second EV in a fleet of EVs managed by the fleet management system, the second EV available to complete an assignment of the EV; and
transmitting instructions to the second EV to complete the assignment of the EV.

19. The method of claim 16, wherein the second location is a location of an EV facility for servicing the battery.

20. The method of claim 16, wherein the update comprises at least one of an updated sensor reading from one of the plurality of sensors, an operational status of the battery, and the current location of the EV at the second time.

* * * * *